United States Patent
Heida

(10) Patent No.: US 7,557,257 B2
(45) Date of Patent: Jul. 7, 2009

(54) METHOD FOR THE SEPARATION OF A CRUDE $C_4$ CUT

(75) Inventor: Bernd Heida, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 403 days.

(21) Appl. No.: 10/565,209

(22) PCT Filed: Jul. 22, 2004

(86) PCT No.: PCT/EP2004/008192

§ 371 (c)(1),
(2), (4) Date: Jan. 20, 2006

(87) PCT Pub. No.: WO2005/009931

PCT Pub. Date: Feb. 3, 2005

(65) Prior Publication Data

US 2006/0241329 A1  Oct. 26, 2006

(30) Foreign Application Priority Data

Jul. 24, 2003  (DE) ............................... 103 33 756

(51) Int. Cl.
*C07C 7/10* (2006.01)
*B01D 11/04* (2006.01)
(52) U.S. Cl. ............................ 585/833; 585/802; 203/2; 203/44
(58) Field of Classification Search ................ 585/833, 585/802; 202/2, 44
See application file for complete search history.

(56) References Cited

U.S. PATENT DOCUMENTS

| | | | |
|---|---|---|---|
| 3,000,794 A | * | 9/1961 | Tschopp ................. 203/54 |
| 3,803,258 A | * | 4/1974 | Weitz et al. ............. 585/862 |
| 4,128,457 A | * | 12/1978 | Barba et al. ............. 203/29 |
| 4,277,313 A | | 7/1981 | Mehra et al. |

(Continued)

FOREIGN PATENT DOCUMENTS

DE  100 22 465  11/2001

(Continued)

OTHER PUBLICATIONS

Proc. Ethylene Prod. Conf. 5(1996) pp. 631-636.

*Primary Examiner*—Tam M Nguyen
(74) *Attorney, Agent, or Firm*—Oblon, Spivak, McClelland, Maier & Neustadt, P.C.

(57) ABSTRACT

A process for fractionating a crude $C_4$ fraction comprising butanes, butenes, 1,3-butadiene and small amounts of other hydrocarbons including $C_4$-acetylenes, by extractive distillation using a selective solvent, wherein the crude $C_4$ fraction (1) is fed into the middle region of a first extractive distillation column (K I) and the selective solvent (2) is fed into the column at a point above that at which the crude $C_4$ fraction (1) is introduced and a gaseous side stream (3) which comprises the $C_4$-acetylenes together with predominantly the selective solvent and in which the concentration of the $C_4$-acetylenes is below the spontaneous decomposition limit is taken off from the first extractive distillation column (K I) at a point below the feed point for the crude $C_4$ fraction (1) and an overhead stream (5) comprising the components which are less soluble than the $C_4$-acetylenes in the selective solvent is taken off from the top of the first extractive distillation column, is proposed.

7 Claims, 1 Drawing Sheet

U.S. PATENT DOCUMENTS

| | | | |
|---|---|---|---|
| 4,504,692 A * | 3/1985 | Arakawa et al. | 585/633 |
| 4,555,312 A * | 11/1985 | Ogura et al. | 203/29 |
| 4,859,286 A * | 8/1989 | Kaibel et al. | 203/75 |
| 6,040,489 A | 3/2000 | Imai | |
| 2003/0181772 A1 * | 9/2003 | Meyer et al. | 585/324 |
| 2004/0065538 A1 * | 4/2004 | Bohner et al. | 203/2 |

FOREIGN PATENT DOCUMENTS

| | | |
|---|---|---|
| EP | 0 284 971 | 10/1988 |
| WO | 2004/011406 | 2/2004 |

* cited by examiner

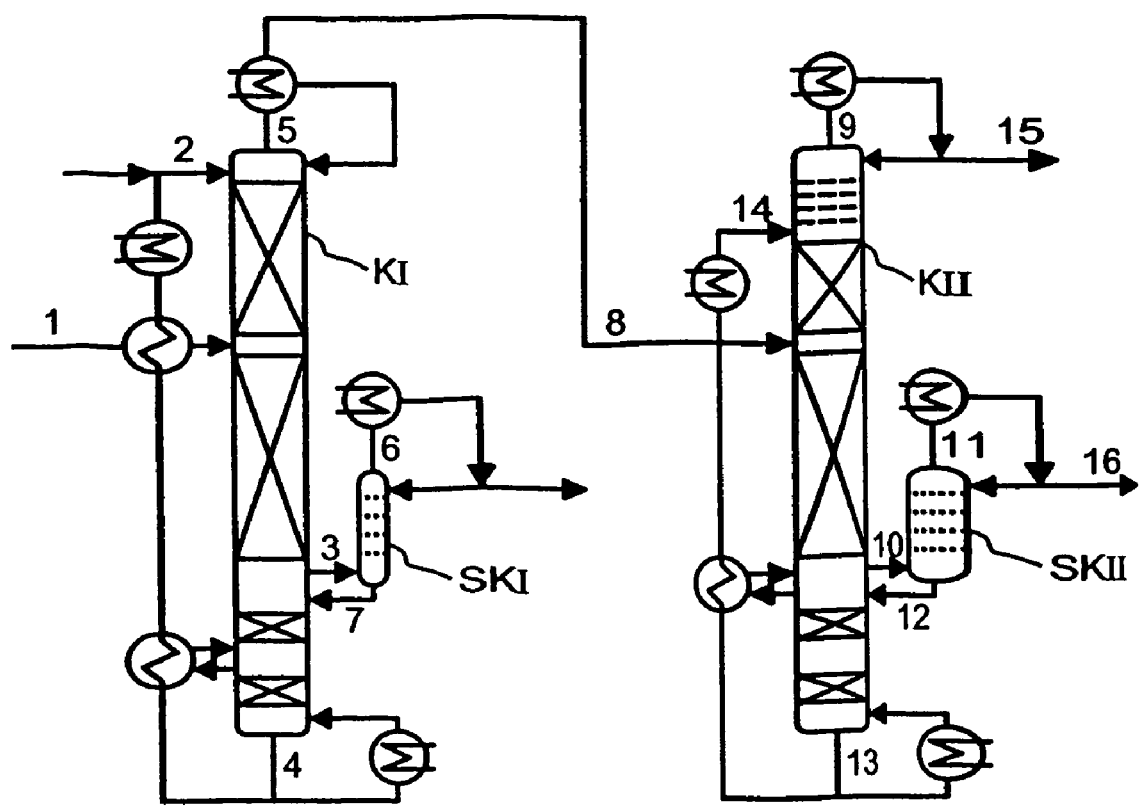

METHOD FOR THE SEPARATION OF A CRUDE $C_4$ CUT

The present invention relates to a process for fractionating a crude $C_4$ fraction by extractive distillation using a selective solvent.

The term $C_4$ fraction refers to mixtures of hydrocarbons having predominantly 4 carbon atoms per molecule. $C_4$ fractions are obtained, for example, in the preparation of ethylene and/or propylene by thermal cracking, for example in steam crackers, in particular naphtha crackers, or FCC plants (fluid catalytic cracking), of a petroleum fraction such as liquefied petroleum gas, naphtha or gas oil. Furthermore, $C_4$ fractions are obtained in the catalytic dehydrogenation of n-butane and/or n-butene. $C_4$ fractions generally comprise butane, n-butene, isobutene, 1,3-butadiene and small amounts of other hydrocarbons including 1,2-butadiene, $C_5$-hydrocarbons and $C_4$-acetylenes(butynes), in particular 1-butyne (ethylacetylene) and butenyne(vinylacetylene). The 1,3-butadiene content of $C_4$ fractions from steam crackers is generally from 20 to 70% by weight, in particular from 35 to 65% by weight, while the content of $C_4$-acetylenes(vinylacetylene and ethylacetylene) generally does not exceed 5% by weight.

Owing to the small differences in the relative volatilities of the components, the fractionation of $C_4$ fractions is a complicated distillation problem. For this reason, fractionation is generally carried out by means of an extractive distillation, i.e. a distillation with addition of a selective solvent (also referred to as extractant) which has a boiling point higher than that of the mixture to be fractionated and which increases the differences in the relative volatilities of the components to be separated.

Many processes for fractionating $C_4$ fractions by means of extractive distillation using selective solvents are known. In all of them, the $C_4$ fraction in gaseous form is conveyed in countercurrent relative to the liquid selective solvent under suitable thermodynamic conditions, generally at low temperatures, frequently in the range from 20 to 80° C., and moderate pressures, frequently from atmospheric pressure to 6 bar, so that the selective solvent becomes laden with the components from the $C_4$ fraction for which it has a greater affinity while the components for which the selective solvent has a lower affinity remain in the vapor phase and are taken off as overhead stream. The components are subsequently liberated individually or as fractions from the laden solvent stream in one or more further process steps under suitable thermodynamic conditions, i.e. at a temperature which is higher and/or a pressure which is lower than in the first process step.

In processes for the thermal fractionation of $C_4$ fractions, $C_4$-acetylenes present therein present particular problems since they are one of the main causes of apparatus fouling and are prone to spontaneous decomposition within wide concentration ranges.

For this reason, processes for fractionating $C_4$ fractions in which the $C_4$-acetylenes are reacted in a first process step by "front-end hydrogenation" have been developed. Front-end hydrogenation has the further advantage that additional product of value, viz. 1-3-butadiene, is obtained as a result of the hydrogenation of the $C_4$-acetylenes.

Such a process is described in Proc.-Ethylene Prod. Conf. 8 (1996), pages 631 to 636. In this process, a high vinylacetylene conversion with a low butadiene loss is achieved using a KLP catalyst, i.e. a catalyst comprising finely divided copper particles on a high-purity γ-aluminum oxide having a defined pore structure as supports, and long catalyst operating lives are also achieved. The upstream selective hydrogenation enables the two-stage butadiene extractive distillation to be simplified to a single-stage process and the apparatus required in the downstream pure distillation to be reduced by one separation column. However, the process has the disadvantage that a separate plant for upstream selective hydrogenation of the acetylene impurities is required.

U.S. Pat. No. 4,277,313 discloses a further process for recovering 1,3-butadiene in which firstly a selective hydrogenation and subsequently an extractive distillation of the 1,3-butadiene are carried out. The selective hydrogenation can be carried out in the liquid phase or the gas phase, in the presence of catalysts of group VIII of the Periodic Table, for example over a palladium/aluminum oxide catalyst. Extractants mentioned are dimethylformamide or diethylformamide, N-methylpyrrolidone, furfural and acetonitrile. The process has, like the process described above, the disadvantage that the upstream selective hydrogenation requires a separate plant.

U.S. Pat. No. 6,040,489 discloses a process for separating 1,3-butadiene from a $C_4$ fraction, in which the $C_4$ fraction is hydrogenated in a column and selectively extracted by means of a solvent, a stream comprising at least the butanes and butenes is taken off from the column as overhead stream and the solvent laden with butadienes is taken off at the bottom and subsequently separated in a solvent stripping column into a butadiene-containing overhead stream and a solvent-containing bottom stream.

The butadiene-containing overhead stream is separated in a butadiene distillation column into a 1,3-butadiene-containing overhead stream and a 1,2-butadiene-containing bottom stream.

In the process of DE-A 100 22 465.2, a $C_4$ fraction is subjected to an extractive distillation and a selective hydrogenation over a heterogeneous catalyst in a dividing wall column or in thermally coupled columns to give a crude 1,3-butadiene stream.

The known front-end processes for removing $C_4$-acetylenes from $C_4$ fractions by selective hydrogenation over heterogeneous catalysts have the disadvantage that not inconsiderable catalyst costs have to be expended and the known catalysts frequently do not have long operating lives. A particularly critical aspect is that when the catalyst becomes exhausted, the entire plant for thermal separation of the $C_4$ fraction has to be shut down.

It is an object of the invention to provide a process for the front-end removal of $C_4$-acetylenes from $C_4$ fractions which does not have the abovementioned disadvantages.

We have found that this object is achieved by a process for fractionating a crude $C_4$ fraction comprising butanes, butenes, 1,3-butadiene and small amounts of other hydrocarbons including $C_4$-acetylenes, 1,2-butadiene and $C_5$-hydrocarbons by extractive distillation using a selective solvent, wherein the crude $C_4$ fraction is fed into the middle region of a first extractive distillation column and the selective solvent is fed into the column at a point above that at which the crude $C_4$ fraction is introduced. A gaseous side stream which comprises the $C_4$-acetylenes together with 1,3-butadiene, 1,2-butadiene, $C_5$-hydrocarbons and selective solvent and in which the concentration of the $C_4$-acetylenes is below the spontaneous decomposition limit is taken off from the first extractive distillation column at a point below the feed point for the crude $C_4$ fraction and an overhead stream comprising the components of the $C_4$ fraction which are less soluble than the $C_4$-acetylenes in the selective solvent is taken off from the top of the first extractive distillation column.

It has been found that it is economically advantageous and possible in process engineering terms to set operating conditions in an extractive distillation column, in particular in respect of the type of selective solvent, the quantity thereof, temperature, pressure and number of theoretical plates, which enable the $C_4$-acetylenes, i.e. the components of the $C_4$ fraction for which the selective solvent has the greatest affinity, to be separated off selectively. This entails process conditions which are unusual for extractive distillation.

A typical crude $C_4$ fraction from a naphtha cracker has the following composition in percent by weight:

| | |
|---|---|
| Propane | 0-0.5 |
| Propene | 0-0.5 |
| Propadiene | 0-0.5 |
| Propyne | 0-0.5 |
| n-Butane | 3-10 |
| i-Butane | 1-3 |
| 1-Butene | 10-20 |
| i-Butene | 10-30 |
| trans-2-Butene | 2-8 |
| cis-2-Butene | 2-6 |
| 1,3-Butadiene | 35-65 |
| 1,2-Butadiene | 0.1-1 |
| Ethylacetylene | 0.1-2 |
| Vinylacetylene | 0.1-3 |
| C5 | 0-0.5 |

Crude $C_4$ fractions from naphtha crackers thus comprise predominantly butanes, butenes and 1,3-butadiene. In addition, small amounts of other hydrocarbons are present. $C_4$-acetylenes are frequently present in a proportion of 5% by weight or else up to 2% by weight.

Selective solvents suitable for the extractive distillation which has been described at the outset are generally substances or mixtures which have a boiling point higher than that of the mixture to be fractionated and have a greater affinity for conjugated double bonds and triple bonds than for simple double bonds and single bonds, preferably dipolar, particularly preferably dipolar aprotic, solvents. To simplify the choice of apparatus, noncorrosive or relatively noncorrosive substances are preferred.

Examples of suitable selective solvents for the process of the present invention are butyrolactone, nitriles such as acetonitrile, propionitrile, methoxypropionitrile, ketones such as acetone, furfural, N-alkyl-substituted lower aliphatic acid amides, such as dimethylformamide, diethylformamide, dimethylacetamide, diethylacetamide, N-formylmorpholine, N-alkyl-substituted cyclic acid amides(lactams) such as N-alkylpyrrolidones, in particular N-methylpyrrolidone. In general, N-alkyl-substituted lower aliphatic acid amides or N-alkyl-substituted cyclic acid amides are used. Particularly advantageous selective solvents are dimethylformamide, acetonitrile, furfural and, in particular, N-methylpyrrolidone.

However, it is also possible to use mixtures of these solvents with one another, for example N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n-butyl or isobutyl tert-butyl ether.

A particularly useful solvent is N-methylpyrrolidone, preferably in aqueous solution, in particular with from 8 to 10% by weight of water, particularly preferably 8.3% by weight of water.

There are in principle no restrictions regarding the columns which can be used for carrying out the extractive distillation.

The $C_4$ fraction is fed into the column in its middle region and the selective solvent is fed in above the point at which the $C_4$ fraction is introduced.

The column is provided with separation-active internals. These can be of any known type. Preference is given to one or more trays being located above the feed point for the selective solvent.

According to the present invention, a side stream comprising the $C_4$-acetylenes together with 1,3-butadiene, 1,2-butadiene, $C_5$-hydrocarbons and selective solvent is taken off in gaseous form from the first extractive distillation column, with the column being operated in such a way that the concentration of the $C_4$-acetylenes in the gaseous side stream is below the spontaneous decomposition limit of these. Dilution to below 30 mol% of $C_4$-acetylenes is generally sufficient for this purpose.

The selective solvent is present in the gaseous side stream in a proportion corresponding to the thermodynamic equilibrium. The side column is operated as a pure rectification column and serves to recover the selective solvent. It has to be operated so that sufficient dilution of the acetylenes to below the spontaneous decomposition region is ensured at every point in the column.

At the top of the first extractive distillation column, an overhead stream comprising the components of the $C_4$ fraction which are less soluble than the $C_4$-acetylenes in the selective solvent is taken off. This stream is preferably condensed in a condenser at the top of the column, and part of it is returned as runback to the column while the remainder is worked up further, preferably in a second extractive distillation column. Partial condensation in which the condensed portion serves as runback to the column and the gaseous portion is fed as feed stream to a second extractive distillation column in which separation into raffinate 1 and crude 1,3-butadiene is carried out is particularly advantageous energetically.

The bottom stream from the first extractive distillation column, which comprises predominantly the selective solvent, is preferably used for heat integration into the first extractive distillation column, condensed and recycled to the first extractive distillation column.

To achieve heat integration, it is possible to cool the hot bottom stream from the first extractive distillation column by means of the crude $C_4$ fraction. In addition or as an alternative, liquid or a substream of the liquid can be taken off from the first extractive distillation column at a theoretical plate which is one or more theoretical plates below the point at which the gaseous side stream is taken off, the liquid is heated and/or vaporized by indirect heat exchange with the bottom stream from the first extractive distillation column and is returned to the first extractive distillation column on the same theoretical plate or above this point, with the theoretical plate from which the liquid or liquid substream is taken off being chosen so that the energy requirement for the first extractive distillation column is minimized.

Here, the term raffinate 1 refers in a known manner to a stream comprising butanes and butenes.

The term crude 1,3-butadiene refers to a hydrocarbon mixture in which the desired product 1,3-butadiene is present in a proportion of at least 90% by weight, preferably at least 95% by weight, particularly preferably at least 98% by weight, balance impurities.

With regard to the separation-active internals, what has been said in the context of the first extractive distillation column applies analogously to the second extractive distillation column.

From the second extractive distillation column, a stream is preferably taken off at the top or in the vicinity of the top of the column, condensed in a condenser and the condensate is partly returned as runback to the second extractive distillation column while the remainder is taken off as raffinate 1.

A side stream is taken off from the second extractive distillation column and selective solvent is preferably separated off from this by feeding the side stream into a second short side column where it is separated into selective solvent which is recycled to the second extractive distillation column and an overhead stream which is condensed in a condenser at the top of the column and partly returned as runback to the column while the remainder is taken off as pure 1,3-butadiene.

Heat integration can be achieved in the second extractive distillation column in a manner analogous to the first extractive distillation column by taking off liquid or a substream of the liquid from the second extractive distillation column at a theoretical plate which is one or more theoretical plates below the side offtake, heating and/or vaporizing it by indirect heat exchange with the bottom stream from the second extractive distillation column and returning it to the second extractive distillation column on the same theoretical plate or above this, with the theoretical plate from which the liquid or liquid substream is taken off being chosen so that the energy requirement for the second extractive distillation column is minimized.

The invention is illustrated below with the aid of a drawing and an example.

The single FIGURE schematically shows a plant according to the invention for fractionating a $C_4$ fraction by extractive distillation.

A crude $C_4$ fraction, stream 1, is fed into the middle region of a first extractive distillation column K I and selective solvent, stream 2, is fed into the column above the point at which the crude $C_4$ fraction is introduced. A gaseous stream 3 comprising $C_4$-acetylenes is taken off at a side offtake below the feed point for stream 1 and this is fed to a first side column SK I. In the side column SK I, the stream 3 is separated by distillation into an overhead stream 6 comprising the acetylenes and a bottom stream 7 which comprises selective solvent and is recycled to the first extractive distillation column K I.

The bottom stream 4 from the first extractive distillation column K I, which comprises predominantly selective solvent, is utilized for heat integration with a liquid stream taken off from the lower region of the first extractive distillation column K I and for preheating the crude $C_4$ fraction, stream 1, condensed and cooled and returned to the first extractive distillation column K I.

The overhead stream 5 from the first extractive distillation column is partially condensed in a condenser at the top of the column, the condensate is returned as runback to the column and the gaseous portion is taken off as stream 8.

In the second extractive distillation column K II, the stream 8 is conveyed in countercurrent to the selective solvent, stream 14, and separated by distillation into an overhead stream 9 which is condensed and part of it is returned as runback to the column K II and the remainder is taken off as raffinate 1, stream 15, and a side stream 10 from which crude 1,3-butadiene is obtained after the solvent has been separated off in a second short side column SK II. In the second side column SK II, the side stream 10 is separated into an overhead stream 11 which is condensed in a condenser at the top of the column and part of it is returned as runback to the column and the remainder is taken off as crude 1,3-butadiene, stream 16, and a bottom stream 12 which comprises predominantly the selective solvent and is recycled to the second extractive distillation column K II. At the bottom of the second extractive distillation column K II, a bottom stream 13 is taken off, utilized for heat integration with the liquid stream from the lower region of the second extractive distillation column K II, condensed and subsequently returned as stream 14 to the second extractive distillation column.

EXAMPLE

A crude $C_4$ stream, reference 1 in the FIGURE, comprising the following components present in amounts of more than 0.01% by weight in each case:

| | |
|---|---|
| n-butane | 5.75 |
| i-butane | 2.45 |
| 1-butene | 13.89 |
| i-butene | 25.65 |
| trans-2-butene | 4.44 |
| cis-2-butene | 2.96 |
| 1,3-butadiene | 43.84 |
| 1,2-butadiene | 0.14 |
| ethylacetylene | 0.13 and |
| vinylacetylene | 0.74, | is fed at a flow rate of 32 t/h into an extractive distillation column K I having 28 theoretical plates, numbered from the top, on the 15th theoretical plate.

The column is operated at a pressure at the top of 4.5 bar absolute and a temperature at the top of 58.8° C.

120 t/h of the extractive solvent N-methylpyrrolidone (NMP), containing 8.3% by weight of water, stream 2, is fed in on the upper plate of the extractive distillation column K I.

A stream having a flow of 224 kg/h, reference 3 in the FIGURE, and comprising the following components present in amounts of more than 0.01% by weight in each case:

| | |
|---|---|
| 1,3-butadiene | 2.45 |
| 1,2-butadiene | 1.21 |
| ethylacetylene | 1.67 |
| vinylacetylene | 10.40 |
| water | 70.10 and |
| NMP | 14.08, | is taken off from the third theoretical plate.

The solvent is washed out of this stream in the side column SK I, which is operated as a pure rectification column, by means of the runback. This gives an overhead stream, reference 6 in the FIGURE, comprising the following components present in amounts of greater than 0.01% by weight in each case:

| | |
|---|---|
| 1,3-butadiene | 3.24 |
| 1,2-butadiene | 1.60 |
| ethylacetylene | 2.20 |
| vinylacetylene | 13.56 |
| $C_5$-hydrocarbons | 0.16 and |
| water | 79.24. |

The extractive solvent N-methylpyrrolidone which has been purchased at considerable cost is completely separated off except for 1 ppm in the overhead stream from the side column and is returned to the first extractive distillation column K I. In this way the acetylenes (ethylacetylene, vinylacetylene) can be removed from the process essentially without losses of the expensive component N-methylpyrrolidone via the overhead stream of the side column SK I.

I claim:

1. A process for fractionating a crude $C_4$ fraction comprising butanes, butenes, 1,3-butadiene and small amounts of other hydrocarbons including $C_4$-acetylenes, 1,2-butadiene and $C_5$-hydrocarbons by extractive distillation using a selective solvent, the process comprising feeding the crude $C_4$ fraction into a middle region of a first extractive distillation column and feeding the selective solvent into the column at a point above where the crude $C_4$ fraction is fed taking off a gaseous side stream from the first extractive distillation column at a point below the feed point for the crude $C_4$ fraction, wherein the gaseous side stream comprises the $C_4$-acetylenes, 1,3-butadiene, 1,2-butadiene, $C_5$-hydrocarbons and selective solvent; and wherein the concentration of the $C_4$-acetylenes in the gaseous side stream is below a spontaneous decomposition limit;

taking off an overhead stream comprising components of the crude $C_4$ fraction which are less soluble than the $C_4$-acetylenes in the selective solvent from the top of the first extractive distillation column;

feeding the gaseous side stream to a first side column in which the gaseous side stream is separated into an overhead stream and a bottom stream, wherein the overhead stream comprises the $C_4$-acetylenes and is condensed in a condenser at the top of the first side column;

a part of the condensed overhead stream is returned as runback to the first side column, and returning the bottom stream which comprises the selective solvent to the first extractive distillation column.

2. The process as claimed in claim 1, further comprising
condensing the overhead stream from the first extractive distillation column in a condenser at the top of the first extractive distillation column, and wherein part of the condensed overhead stream is returned as runback to the first extractive distillation column while the remainder of the condensed overhead stream is fed to a second extractive distillation column in which the remainder of the condensed overhead stream is separated into raffinate 1 and crude 1,3-butadiene.

3. The process as claimed in claim 2, further comprising
partially condensing the overhead stream in the condenser at the top of the first extractive distillation column to yield a condensed portion and a gaseous portion; and returning the condensed portion of the overhead stream from the first extractive distillation column as runback to the first extractive distillation column and feeding the gaseous portion of overhead stream to the second extractive distillation column.

4. The process as claimed in claim 2, further comprising
taking off an overhead stream from the second extractive distillation column;

condensing the overhead stream in a condenser, wherein part of the condensed overhead stream is returned to the second extractive distillation column as runback while the remainder of the condensed overhead stream is taken off as raffinate 1, taking off a side stream from the second extractive distillation column below the feed point for the condensed overhead stream from the first extractive distillation column.

5. The process as claimed in claim 4, further comprising
feeding the side stream taken off from the second extractive distillation column is fed to a second side column;

separating that side stream into an overhead stream,
condensing the overhead stream,
returning a part of the condensed overhead stream as runback to the second side column, taking off the remainder of the condensed overhead stream as a crude 1,3-butadiene stream; and returning the remainder of the condensed overhead stream as a crude 1,3-butadiene stream and a bottom stream which comprises the selective solvent to the second extractive distillation column.

6. The process as claimed in claim 2, further comprising
taking off a liquid or a substream of the liquid from the second extractive distillation column at a theoretical plate, which is one or more theoretical plates below the side stream offtake of the second extractive distillation column;

heating and/or vaporizing the liquid by indirect heat exchange with the bottom stream from the second extractive distillation column; and returning the heated and/or vaporized liquid to the second extractive distillation column on the same theoretical plate or above, with the theoretical plate from which the liquid or liquid substream is taken off being chosen so that the energy requirement for the second extractive distillation column is minimized.

7. A process for fractionating a crude $C_4$ fraction comprising butanes, butenes, 1,3-butadiene and small amounts of other hydrocarbons including $C_4$-acetylenes, 1,2-butadiene and $C_5$-hydrocarbons by extractive distillation using a selective solvent, the process comprising feeding the crude $C_4$ fraction into a middle region of a first extractive distillation column and feeding the selective solvent into the column at a point above where the crude $C_4$ fraction is fed taking off a gaseous side stream from the first extractive distillation column at a point below the feed point for the crude $C_4$ fraction, wherein the gaseous side stream comprises the $C_4$-acetylenes, 1,3-butadiene, 1,2-butadiene, $C_5$-hydrocarbons and selective solvent; and wherein the concentration of the $C_4$-acetylenes in the gaseous side stream is below a spontaneous decomposition limit; and taking off an overhead stream comprising components of the crude $C_4$ fraction which are less soluble than the $C_4$-acetylenes in the selective solvent from the top of the first extractive distillation column;

taking off a bottom stream from the first extractive distillation column, cooling the bottom stream by indirect heat exchange with the crude $C_4$ fraction, condensing the bottom stream in a condenser; and returning the condensed bottom stream to the first extractive distillation column;

taking off a liquid or a substream of the liquid from the first extractive distillation column at a theoretical plate, which is one or more theoretical plates below the point at which the gaseous side stream is taken off, heating and/or vaporizing the liquid by indirect heat exchange with the bottom stream from the first extractive distillation column; and returning the heated and/or vaporized liquid to the first extractive distillation column at the same theoretical plate or above, wherein the theoretical plate from which the liquid or liquid substream is taken off being chosen so that the energy requirement for the first extractive distillation column is minimized.

* * * * *